United States Patent [19]

Sherrington et al.

[11] Patent Number: 4,965,289

[45] Date of Patent: Oct. 23, 1990

[54] SUBSTRATE AND PROCESS FOR MAKING A SUBSTRATE

[75] Inventors: David C. Sherrington, Kirkintilloch, Scotland; Philip W. Small, Merseyside, United Kingdom

[73] Assignee: Unilever Patent Holdings B.V., Rotterdam, Netherlands

[21] Appl. No.: 185,672

[22] Filed: Apr. 25, 1988

[30] Foreign Application Priority Data

Apr. 24, 1987 [GB] United Kingdom ............... 8709689
Nov. 24, 1987 [GB] United Kingdom ............... 8727474

[51] Int. Cl.$^5$ .............................................. C08J 9/36
[52] U.S. Cl. ..................................... 521/53; 521/61; 521/62; 521/63; 521/64
[58] Field of Search .................... 521/61, 62, 63, 64, 521/53

[56] References Cited

U.S. PATENT DOCUMENTS

| | | | |
|---|---|---|---|
| Re. 27,444 | 7/1972 | Will | 521/62 |
| 3,763,056 | 10/1973 | Will | 521/62 |
| 3,822,224 | 7/1974 | Gillan | 521/63 |
| 3,879,314 | 4/1975 | Gunning et al. | 521/62 |
| 3,891,577 | 6/1975 | Kershaw et al. | 521/62 |
| 3,923,704 | 12/1975 | Gunning et al. | 521/62 |
| 3,933,579 | 1/1976 | Kershaw et al. | 521/62 |
| 3,991,017 | 11/1976 | Barrett et al. | 260/2.1 R |
| 4,192,798 | 3/1980 | Verlander et al. | 260/112.5 R |
| 4,399,237 | 8/1983 | Morrison, Jr. | 521/64 |
| 4,461,848 | 7/1984 | Lawson et al. | 521/64 |
| 4,522,953 | 6/1985 | Barby et al. | 521/64 |
| 4,551,482 | 11/1985 | Tschang et al. | 521/53 |
| 4,612,334 | 9/1986 | Jones et al. | 521/147 |
| 4,797,425 | 1/1989 | Kishimo | 521/64 |

FOREIGN PATENT DOCUMENTS

| | | |
|---|---|---|
| 0041934 | 12/1981 | European Pat. Off. . |
| 0048110 | 3/1982 | European Pat. Off. . |
| 060138 | 9/1982 | European Pat. Off. . |
| 2024586 | 8/1970 | France . |
| 1210656 | 10/1970 | United Kingdom . |
| 1421531 | 1/1976 | United Kingdom . |
| 1521128 | 8/1978 | United Kingdom . |
| 1570485 | 7/1980 | United Kingdom . |
| 1574414 | 9/1980 | United Kingdom . |
| 1600241 | 10/1981 | United Kingdom . |

OTHER PUBLICATIONS

Kun et al., "The Pore Structure of Macroreticular Ion Exchange Resins" *Journal of Polymer Science:Part C*, No. 16, pp. 1157–1169 (1967).
Dryland et al., *J. Chem. Soc. Perkin Trans. I*, pp. 125–137.
Epton et al., *Int. J. Biol. Macromol.*, 7:289–298 (1985).

*Primary Examiner*—Morton Foelak
*Attorney, Agent, or Firm*—Cushman, Darby & Cushman

[57] ABSTRACT

A substrate comprises a porous polymeric material having a porosity of at least 75% and comprising pores having a diameter within the range 1 to 100 μm and being interconnected by a plurality of holes, and a gel or material adapted in use to form a gel which gel or pre-gel materials is contained and retained within the pores of the polymeric material and is adapted in use to interact with a reactive species and can be made by depositing and retaining the gel or a material adapted in use to form the gel within the pores of the porous polymeric material. The high porosity of the porous polymeric material in combination with the retention of the gel within the pores permit high loading capacities, particularly in the area of peptide synthesis to be achieved. The substrate can be employed in chemical synthesis, chromatography techniques, ion exchange and separation techniques.

14 Claims, No Drawings

SUBSTRATE AND PROCESS FOR MAKING A SUBSTRATE

The present invention relates to novel substrates, processes for making them and uses for them, including synthesizing chemical compounds and chromatography.

A variety of chromatographic techniques and methods of chemical synthesis employ some form of substrate. In a simple batchwise operation the substrate is contained in a vessel and interacted sequentially with added reagents which are then removed by filtration and thorough washing. In a continuous or semi-continuous process the substrate is in the form of a bed such as a column and various reagents are sequentially passed through the bed.

Continuous and semi-continuous techniques thus usually offer advantages over batchwise operation in terms of ease of operation, but can nonetheless suffer problems related to volume change in the bed resulting in pressure changes in the through-flow through the column. Such problems can be particularly acute where the substrate involves some form of gel. A discussion of these problems in the area of solid-phase synthesis is contained in Dryland and Sheppard J. Chem. Soc. Perkin Trans. I 1986 p.125 to 137. An additional relevant publication in this area is Epton, Marr, McGinn, Small, Wellings and Williams Int. J. Biol. Macromol 1985 7 p.289 to 298. It is known as explained in the first of these publications to provide in the case of gel substrate a rigid framework to enclose the gel polymer, so constructed so as to maintain channels for liquid flow and yet permit diffusion of reactants into and out of the gel matrix.

U.S. Pat. No. 3991017 (Rohm and Haas Company) describes a substrate for use in ion exchange resins in which a gel type, crosslinked copolymer at least partially fills the macropores of a macroreticular ion exchange resin. Typically the macroreticular polymers have a surface area of at least 1 sq. meter per gram, more generally at least 5 sq. meters per gram, and have pores larger than about 15 to 20 Å units. The macroreticular polymers are conventionally in bead form usually in an overall particle size of about 10 to 900 microns. At least 5 parts by weight of gel forming components up to a maximum of 300 parts by weight of gel copolymer per 100 parts by weight of macroreticular base polymer are suitably used.

UK No. 1574414 (United Kingdom Atomic Energy Authority) describes a composite material comprising a plurality of discrete particles of a porous rigid support material having a deformable gel within the pore structure of the particles. The particles are discrete porous particles of inorganic material such as natural diatomaceous earth.

It is an object of the present invention to provide an improved substrate for use in for example solid phase synthesis, chromatography and ion exchange applications. It is a further object of the present invention to provide such a substrate allowing improved loading factors to be achieved.

According to a first aspect of the present invention there is provided a substrate comprising a porous polymeric material having a porosity of at least 75% and comprising pores having a diameter within the range 1 to 100 $\mu$m and being interconnected by a plurality of holes, and a gel or material adapted in use to form a gel which gel or pre-gel material is contained and retained within the pores of the polymeric material and is adapted in use, to interact with a reactive species.

The interaction between the gel and a reactive species will be selected having regard to the desired use of the composite substrate. In the case of chemical synthesis the interaction is suitably that of chemical binding and the gel is suitably adapted.

By use of the present invention a substrate is provided in which as in the case of synthesis the gel is capable of a loading of reactive residues up to 5mmol of chemical compound synthesized per g of composite substrate. The gel is suitably a highly solvent swollen cross-linked gel and can for example be a soft deformable polyamide gel. Examples of other gels that can be employed include polystyrenes, saccharose, dextrans, polyacryloylmorpholine, polyacrylates, polymethylacrylates, polyacrylamides, polyacrylolpyrrolidone, polyvinylacetates, polyethyleneglycol, agaroses, sepharose, other conventional chromatography type materials and derivatives and mixtures thereof. Preferably the highly porous material has a pore volume of 75 to 98%, more preferably 85 to 98%, even more preferably 90 to 95%. Suitably the material is a cross-linked polymeric material. On a weight for weight basis the ratio of swollen gel to porous material can range from 60:40 to 95:5 swollen gel:porous material more preferably from 75:25 to 95:5, with a preferred ratio being about 80:20.

The porous material can be in particulate form, preferably of a particle size between 125 and 1500 $\mu$m, more preferably between 250 and 850 $\mu$m, and can for example be the cross-linked vinyl material described in U.S. Pat. No. 4,522,953 or a highly porous cross-linked polycondensation polymeric material described in our co-pending application GB No. 8709688. Both of these porous materials have a high pore volume and can have pores within the range of approximately 1 to 100 $\mu$m, preferably 1 to 50 $\mu$m. Materials made by the processes described in U.S. Pat. No. 4,522,953 or GB No. 8709688 are particularly suitable for use in the present invention as they are highly porous and can consist of regularly formed fully interconnecting cells. Such a combination of features provides a structure that can show rapid uptake of fluids and relatively unobstructed flow through the matrix. These porous structures are suitably made by means of a high internal phase emulsion and thus have the advantage that they can be reproducibly engineered to provide a range of cell sizes and interconnecting holes. Preferably the porous polymeric materials are cross-linked to an extent such that they do not swell to more than twice their dry bed volume in use. Throughout the present specification porosity values and pore size measurements refer to the porous polymeric material in the unswollen state.

Preferably the gel is formed in situ in the pores of the porous material. The particulate porous material can be admixed with a solution which permeates the open interconnecting pores of the particulate material and forms therein the gel. The resulting material is preferably placed, or can be made in, in a column in order to provide an appropriate through flow system for example in performing a chemical synthesis. Alternatively the porous material can be in monolithic block form and the gel can be formed in situ following permeation into the interconnecting pores of the block.

According to a second aspect of the present invention, there is provided a process for preparing a substrate comprising depositing and retaining a gel or a material adapted in use to form a gel within the pores of a porous polymeric material having a porosity of at least 75% and comprising pores having a diameter within the range 1 to 100 μm and being interconnected by a plurality of holes, the gel being adapted in use to interact with a reactive species.

Preferably the process includes forming the gel within the pores of the porous material. More preferably the process includes forming the gel within the pores of the porous material and simultaneously retaining the gel during its formation within the pores of the porous material. The gel can for example be made by the conventional polymerization and co-polymerization routes to form gels, for example free-radical vinyl polymerization, poly-condensation reactions, and cross-linking of soluble linear polymers.

The gel and the porous polymeric materials are suitably those mentioned above. In particular we have found that use of porous polymeric materials as described in U.S. Pat. No. 4,522,953 or GB No. 8709688 having interconnected pores allows ready access of the gel materials into within the pores and subsequent ready access of reactive species in use.

Preferably the process includes forming the gel within the pores of the porous material. Preferably retention of the gel within the pores is by a chain entanglement and/or interpenetration between the gel and the surface of the porous polymeric material and/or by a process that is believed to involve chemically binding the gel to the surface of the pores of the porous material. Thus preferably the process includes depositing and retaining the gel within the pores of the porous polymeric material by subjecting porous cross-linked polymeric material to a solution comprising a swelling solvent for the porous polymeric material and gel precursor materials, allowing the gel precursor materials to permeate the swollen polymeric material and forming the gel from the gel precursor materials within the pores. Preferably the process additionally or alternatively includes depositing and retaining the gel within pores of the porous polymeric material having reactive groups thereupon by allowing gel precursor materials to permeate the pores of the polymeric material and forming the gel from the gel precursor materials within the pores and simultaneously allowing the gel and/or gel precursor to react with the reactive groups on the pores of the porous polymeric material.

In the mode of retention comprising chain entanglement/interpenetration a porous cross-linked polymeric material is suitably employed which is mixed with the precursors for forming the gel in the presence of a swelling agent for the polymeric material. As the gel precursors permeate the porous polymeric material, the porous material swells and entraps the contactable portion of the forming cross-linked swollen gel material by polymer chain interpenetration between the swollen polymeric polymer material and the forming cross-linked swollen gel. Cross-linking of the porous polymeric material to the extent that it can swell up to twice its dry bed volume has been found appropriate. Suitable swelling solvents will depend on the nature of the porous polymeric material. For polystyrene for example suitable solvents would be halocarbons such as dichloroethane, dichloromethane, chloroform, and toluene and tetrahydrofuran. The gel material is suitably the monomer precursors which permeate the pores and polymerize in situ leading to the chain entanglement and interpenetration.

Where retention is believed to occur by chemical bonding between the highly porous material and the material described in use to be in the form of a gel the chemical bonding can be achieved by reaction between the gel ready formed and reactive groups on the porous material and/or reaction with reactive groups on the porous material during gel formation. An example of this latter technique is vinyl polymerization to form the gel and simultaneous attachment via a reactive group on the porous material. References throughout the specification to chemical binding between the gel and the porous polymeric material are to be interpreted as the believed mechanism having regard to the evidence given below.

The porous material can be made with the reactive groups ready in situ or can be treated subsequent to preparation to contain the reactive groups. Appropriate reactive groups include vinyl, aminomethyl and carboxyl.

Evidence indicating a slight difference in performance between these two modes of effecting retention is given as follows, showing a preference for the binding route and indicating that the binding is probably chemical co-valent binding. For each embodiment a sample of substrate was prepared and the yield of composite substrate relative to the starting materials was calculated. For the chain entanglement mode with swelling of the porous polymeric material 70% retention of gel in the composite substrate was achieved. For the presumed binding route 100% inclusion of the gel was achieved, indicating complete retention of the gel by the porous material. For comparison mere permeation of the gel into the porous polymeric material with no active steps to effect its retention resulted in 0% inclusion of gel following conventional washing steps.

According to another aspect of the present invention there is provided a substrate comprising a highly porous polymeric material having a porosity of at least 75% and comprising pores having a diameter within the range 1 to 100 μm and being interconnected by a plurality of holes, wherein reactive groups are chemically bound to the pore surfaces and are adapted in use to interact, e.g. by binding chemically, with a reactive species. Suitable porous materials are disclosed in U.S. Pat. No. 4,522,953 and in our co-pending application mentioned above and have pore sizes preferably in the range 1 to 50 μm. Preferably the materials are cross-linked and have a porosity of 75 to 98%, more preferably 85 to 98%, even more preferably 90 to 95%. Materials made by the process described in U.S. Pat. No. 4,522,953 or GB No. 8709688 specifications are particularly suitable for use in the present invention as they are highly porous and can consist of regularly formed fully interconnecting cells. Such a combination of features provides a structure that can show rapid uptake of fluids and relatively unobstructed flow through the matrix. These porous structures are suitably made by means of a high internal phase emulsion and thus have the advantage that they can be reproducibly engineered to provide a range of cell sizes and interconnecting holes. The porous polymeric material can be employed in particle, sheet or monolithic block form. The porous material can be made with the reactive groups already in situ e.g. vinyl groups on a polyvinyl porous material or can be treated subsequent to preparation to provide the reactive groups e.g. aminomethyl groups. If desired the reactive groups can be further reacted to provide spacer groups which subsequently interact with the reactive species.

According to another aspect of the present invention there is provided a use of the present substrates wherein a reactive species is passed through the substrate, preferably under flow conditions, and interacts with the reactive substrate.

Examples of use of the present method include: chemical synthesis including peptide synthesis, oligonucleotide synthesis, oligosaccharide synthesis, and monoclonal synthesis; chromatography; ion exchange; and separation techniques including gel electrophoresis. In chemical synthesis a first species can be passed through the substrate and then further reactive species can be passed sequentially through the substrate so as to react with the reactive residue then present and chemically attached to the substrate. Eventually the final chemical assembly can be detached and removed from the substrate. The present process can thus be particularly suitable for the synthesis of peptides.

The substrate can be any of those described above. By means of the present use sequential synthesis can occur at high yield. The chemical nature of the highly swollen gel in a flow through system allows reactive residues to be attached with a high load leading to high yields. In peptide synthesis yields of 0.1 to 5 mmol per g of composite substrate can be achieved.

In the preferred embodiment in which gel is contained and retained within the pores of a highly porous polymeric material the overall substrate can nonetheless be substantially rigid, incompressible and homogeneous. With such a substrate in the form of a packed column flow rates suitable for flow operation can be achieved. Batchwise operation can alternatively be employed.

Moreover in the more preferred embodiment in which the gel is believed chemically bound to the porous polymeric material suitable flow rates can be achieved without the gel being washed out of the porous material or lost into solution.

It is to be understood that the present invention extends to the products of the present processes and uses.

Embodiments of the present invention will now be described by way of example only with reference to the following Examples.

The present invention can be applied to a variety of systems. One system however which is of particular interest is peptide synthesis. The present system is especially applicable to peptide synthesis as it lends itself to repeated sequential reactions at a relatively high throughput rate.

Thus in a peptide synthesis scheme the reactive group (X) is attached to the polymer and is reacted with the first amino acid of the sequence to be synthesized. This first amino acid contains its own protecting group (PG). After deprotection, a further protected amino acid is attached and then the process of deprotection and coupling is repeated until the desired amino acid sequence is produced. The resulting peptide is then detached from the polymer support and can if desired be purified.

Diagrammatically the peptide synthesis scheme can be shown as follows:

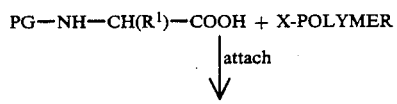

-continued

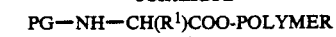

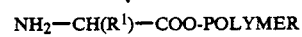

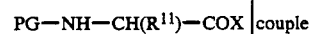

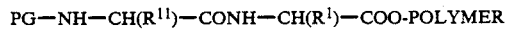

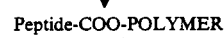

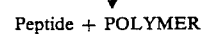

In one embodiment the synthesis takes place within a highly swollen deformable polyamide gel which is polymerized within the pore structure of the polymeric structural material, which is rigid. Diffusion of reactants into and out of the polyamide gel where the reaction takes place can be rapid and negligible pressure develops when the system is for example in the form of a column under normal flow conditions. Synthesis under conditions of flow is preferred as, in general, flow systems offer greater opportunities for analytical control. For example the continuous monitoring of effluent streams by UV-VIS spectrophotometry and other continuous monitoring techniques can be readily achieved and offers the potential for automated feedback control of each synthesis cycle.

EXAMPLE 1

Preparation of Substrate

A cross-linked polyvinyl porous polymeric material formed by the high internal phase emulsion method described in our U.S. Pat. No. 4,522,953 was employed as the structural carrier. It had 90% pore volume, and employed 10% cross-linking agent divinyl benzene and had a density of 0.047 g cm$^{-3}$. The polymeric material was in the form of a milled and sieved powder having a particulate size within the range 850 to 1200 μm. Its pore size was within the range 1 to 50 μm.

The polymeric gel matrix was poly (N-(2-(4-acetoxyphenyl)ethyl)acrylamide). A solution of 2.5 g of the monomer N-(2-(4-acetoxyphenyl)ethyl)acrylamide, 0.075g of the cross-linking agent ethylene bis (acrylamide), 0.1 g of the initiator azobisisobutyronitrile was prepared in 10 cm$^3$ dichloroethane and deoxygenated by purging with nitrogen.

The milled and sieved particulate polymeric material (0.7 g) was added to the solution and polymerization of the acrylamide was initiated by heating the mixture at 60° C. while rotating the sample on a rotary evaporator modified for reflux. The dichloroethane served to swell the porous polymeric material and allow ready penetration of the polyamide monomer and subsequent entrapment and interpenetration of the polymerizing polyamide by the porous polymeric material.

After 1 hour reaction time the resulting composite was washed exhaustively with dimethylformamide and diethyl ether and then vacuum dried. The yield of resulting composite was 2.7 g, the gel being retained within the porous polymeric material due to chain entanglement.

0.25 g of the composite was treated with 5% solution of hydrazine hydrate in dimethylformamide for 5 minutes. This treatment provided free phenolic functionalities within the secondary gel matrix which act as reactive groups (X).

Peptide Synthesis

To commence a peptide synthesis 0.95 g (5.0 mmol) t-butyloxycarbonyl alanine and 1.24 g (6 mmol) dicyclohexylcarbodiimide were dissolved in 10cm$^3$ dimethylformamide and allowed to react for 30 minutes with stirring. This activated form of the thus produced protected amino acid (O-acyl urea) was added to the dried composite substrate (0.25 g), followed by 0.24 g (2.0 mmol) dimethylaminopyridine, and the esterification reaction was allowed to proceed for 24 hours during which time the mixture was agitated by passing through nitrogen in a solid phase reactor. At the end of this time the composite was washed exhaustively with dimethylformamide and diethyl ether. The weight of the loaded composite following the reaction was 0.52 g.

To remove the protection group (PG=t-butyloxycarbonyl) 0.50 g of the loaded composite substrate was retained in the solid phase reactor and 9cm$^3$ benzyl alcohol was added. The suspension was nitrogen stirred for 1 hour allowing sufficient time for the secondary gel matrix to swell in the benzyl alcohol. 1cm$^3$ of the deprotection reagent boron trifluoride etherate was added and the reaction nitrogen stirred for 3 hours. The composite was washed exhaustively with dimethylacetamide and diethyl ether.

In order to carry out continuous flow synthesis the resulting composite was transferred to the column of a Pepsynthesiser Mk2 (ex Cambridge Research Biochemicals), which is a semi-automatic continuous flow peptide synthesizer. The column was initially purged with a solution of 0.2 g (2 mmol) N-methylmorpholine in 50cm$^3$ dimethylformamide to release the free amino terminal groups, followed by a wash through with dimethylformamide.

Further Chain Elongation

The symmetrical anhydride of Fmoc- Proline (PG=Fmoc =fluorenylmethoxycarbonyl) was prepared by reacting 0.80 g Fmoc-Pro-OH (2.4 mmol) with 0.23 g dicyclohexylcarbodiimide in dichloromethane for 30 minutes. The resulting precipitate was removed by filtration. The solvent was evaporated under reduced pressure and the resulting solid dissolved in 3cm$^3$ dimethylformamide.

The solution was drawn into the column of the Pepsynthesiser, which was set to operate in a recirculation mode. After 25 minutes a small sample of the composite substrate was removed from the column, washed with dimethylformamide and ether and subjected to the kaiser test (ninhydrin) for detection of primary amine. The test was negative and therefore the Pepsynthesiser was switched to wash mode utilizing dimethylformamide.

Deprotection

Removal of the Fmoc group was performed by flowing 20% diethylamine in dimethylformamide through the composite for 10 minutes, followed by a wash mode utilizing dimethylformamide.

Two further coupling steps were carried out according to the following sequence of events: (i) couple Fmoc-Alanine (0.74 g 2.4 mmol) (ii) deprotect with 20% piperidine in dimethylformamide (iii) couple Boc-Alanine (0.44 g 2.4 mmol).

The amino acids were reacted, following pre-activation as the symmetrical anhydride, using the procedure given previously and the quantities given above.

Detachment

The composite was removed from the instrument and a 100mg sample was subjected to hydrazinolysis by reaction with 0.1cm$^3$ hydrazine hydrate in 5cm$^3$ dimethylformamide for 2 minutes. The reaction solution was drawn into chilled diethyl ether and the precipitate collected by filtration. The precipitate was washed exhaustively with diethyl ether and vacuum dried. The washed and dried precipitate comprised Boc-Ala-Ala-Pro-Ala-N$_2$H$_3$ in a yield of 61 mg.

Analytical Checks

The product was subject to: thin layer chromatography (Silica gel 60$_{254}$) Propanol: H$_2$O (3:1) Rf=0.78; Chloroform: Methanol (4:1) Rf=0.71 (both homogeneous, single component); and high performance liquid chromatography (Waters Novapak C-18 column): $R_T$=12.5 min (>90%) solvent B water containing 0.1% trifluoroacetic acid; solvent C Acetonitrile containing 0.1% TFA, gradient 100%B to 70%C over 30 minutes.

The Amino acid analysis gave a molar ratios of Ala (2.9) and Pro (1.0).

EXAMPLES 2 AND 3

The present Examples relate to the preparation of a substrate comprising a functionalized porous polymeric material chemically reacted with a gel during the preparation of the gel.

In outline, the preformed porous polymeric material was reacted with N-hydroxymethylphthalimide in the presence of a catalyst (trifluoromethane sulphonic acid, CF$_3$SO$_3$H) to yield a phthalimide derivative which on nucleophilic scission with hydrazine provides the aminomethyl porous polymeric material.

This derivative on reaction with acryloyl chloride provides a porous polymeric material with double bonds at the surface of the pores. On introduction of pre-gel material in the form of monomers into the structure, followed by initiation of polymerization (heat) the surface double bonds of the porous material are assumed also take part in the reaction, producing what is believed to be a gel chemically-linked to the porous polymeric material.

EXAMPLE 2

Preparation of Substrate

A cross-linked polyvinyl porous polymeric material formed by the high internal phase emulsion method described in U.S. Pat. No. 4,522,953 was employed as the starting material for the structural carrier. It had 90% pore volume and a density of 0.047 g cm.$^{-3}$ and was made from a 10:90 mixture of commercial divinylbenzene and styrene. It had pore sizes within the range 10 to 20 μm. The polymeric material was in the form of a milled and sieved powder having a particulate size within the range 425 to 850 μm.

The powdered polymeric material (10 g, 10 mmol), prewashed and ground to size (425 to 850 μm), and N-hydroxymethylphthalimide (5.85 g, 0.03 mol) were placed in a three neck round bottom flask (500cm³). The resulting resin was suspended in a mixed solvent system of trifluoroacetic acid: dichloromethane (1:2) (total volume 300cm³). Trifluoromethane sulphonic acid (0.9cm³, 0.01 mol) was added, slowly, to the rapidly stirred reaction mixture. Once uniform mixing had been achieved, and the reaction mixture appeared consistent, the stirring was ceased to prevent further fragmentation of the polymeric particles.

The mixture was allowed to stand at room temperature overnight (i.e. 16 hours).

The resin was transferred to a sintered funnel and washed with dichloromethane (2×200cm³) and ethanol (2×200cm³).

The damp phthalimido resin was placed into a three neck round bottom flask) (1 liter). Ethanol (422.5 ml) containing 5% hydrazine (22.5 ml) (total volume 450 ml) was added to the resin and the mixture allowed to reflux, with stirring for sixteen hours. A ninhydrin test after five hours gave a positive result, however, the reaction was allowed to continue. The reaction was terminated after sixteen hours by filtering the resin, whilst hot, and washing with hot ethanol (4×100 ml) and cold methanol (4×100 ml). The resin was placed into a vacuum oven at room temperature and amino methyl polymeric material (10.21 g) of a particulate nature was obtained. The material gave an intense blue color in a final ninhydrin test, indicating a high level of amino groups present.

ACRYLATION OF AMINO METHYL POROUS POLYMERIC MATERIAL USING ACRLOYL CHLORIDE

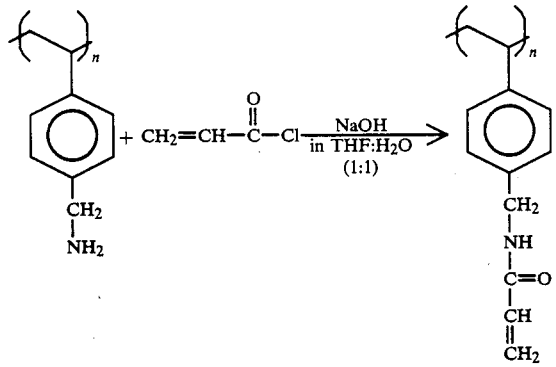

The amino methylated polymeric material (2.0 g, 0.20 mmol) was placed into a round-bottom flask (50 ml), which was situated in a salt/ice bath. Sodium hydroxide (9.28 mg, 0.029 mmol) was dissolved in distilled water (2.5 ml) and this solution was mixed with tetrahydrofuran (THF) (2.5 ml). The mixed solvent system, containing sodium hydroxide, was added to the polymeric material in the flask. Acryloyl chloride (10 ml, 0.12 mol) was added dropwise to the mixture. During this addition, the pH was monitored by spotting the reaction mixture on to full range indicator paper, and maintained at pH>11 by the addition of sodium hydroxide solution, when necessary. After 4 hours a ninhydrin test on the resin was negative, indicating an absence of primary amine.

The reaction was terminated by filtering the reaction mixture and washing with methanol:water (1:1) (3×50 ml) followed by methanol (3×50 ml). The resulting solid was placed in the vacuum oven at room temperature until constant weight had been obtained. A white solid (2.05 g) was obtained.

SYNTHESIS OF N-(2-(4-ACETOXYPHENYL)-ETHYL) ACRYLAMIDE (OR ACRYLOYL TYRAMINE ACETATE)

Using Tyramine Hydrochloride

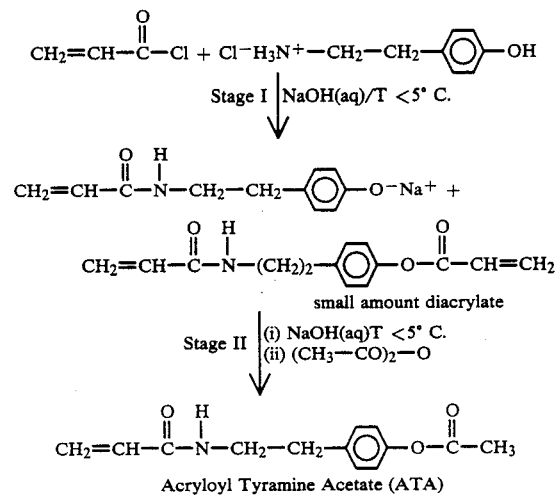

Acryloyl Tyramine Acetate (ATA)

Sodium hydroxide (57.6 ml), 12 mol.dm³, 0.69 mol) was poured into a three neck roundbottom flask (500 ml), equipped with a dropping funnel, overhead electric stirrer and guard tube. Tyramine hydrochloride (25 g, 0.144 mol) was added to the rapidly stirring caustic and an aliquot of the slurry was removed. This sample as subjected to a ninhydrin test, the result of which was positive, as expected, indicating the presence of primary amine groups.

The reaction flask was cooled to 0° C., using a salt-/ice bath, prior to the dropwise addition of acryloyl chloride (14 ml, 0.17 mol) over a period of fifteen minutes. During this addition, the pH of the reaction was monitored by spotting the reaction mixture on to full range indicator paper and maintained at pH 10 by the addition of sodium hydroxide solution as required. The pH was controlled at this level to prevent formation of the diacrylate waste product as much as possible. The mixture was stirred for thirty minutes and another aliquot of the slurry was removed and subjected to a ninhydrin test. Again, the result was positive indicating that the first stage of the reaction had not gone to completion. A second portion of acryloyl chloride (14 ml, 0.17 mol) was added, under controlled pH conditions, as above. The mixture was stirred for a further thirty minutes and subjected to a ninhydrin test for primary amine, which proved to be negative. An equal volume of ethyl acetate was added to the mixture.

Sodium hydroxide solution (26.4 ml, 12 mol.dm⁻³, 0.32 mol) was added and the reaction flask cooled to 0° C., using a salt/ice bath. Rapid stirring was used to achieve effective mixing of the two phases. Acetic anhydride (32.7 ml, 0.35 mol) was added, to the rapidly stirring reaction mixture, over a period of five minutes. During the acetylation, the pH of the reaction was monitored by spotting the reaction mixture onto full range indicator paper and maintained at pH>11 by the addition of sodium hydroxide solution, as required. The pH was controlled at this level in order to prevent back hydrolysis of the acryloyl tyramine acetate (ATA) product. After all the acetic anhydride had been added, the reaction mixture was allowed to settle into two phases. The lower aqueous phase was discarded whereas the upper ethyl acetate was allowed to stand over anhydrous magnesium sulphate for a period, filtered and the solvent removed, using a rotary evaporator. A white solid was produced and washed several times with ether. The final product was a white powder in a yield of 21 g (65%).

The product was subjected to $^1$H nmr analysis. The resulting spectrum showed all the peaks and integral heights expected for acryloyl tyramine acetate.

IMPREGNATION OF DERIVATIZED POROUS POLYMER MATERIAL WITH ACRYLOYL TYRAMINE ACETATE traces of oxygen which would inhibit the subsequent polymerization. The flask was placed on to a rotary evaporator, with a vacuum, allowed to rotate and maintained in a water bath at 60° C. for one hour. The flask was rotated to hinder polymerization on the surface between adjacent polymeric particles and to promote polymerization of ATA within the pores of the polymeric material.

The final product was filtered, washed with DMF (3 times), then ether and was finally dried in the vacuum oven at room temperature.

EXAMPLE 3

The procedure of Example 2 was followed with the exception that acryloyl sarcosine methyl ester was employed in place of acryloyl tyramine acetate

SYNTHESIS OF ACRYLOYL SARCOSINE METHYL ESTER

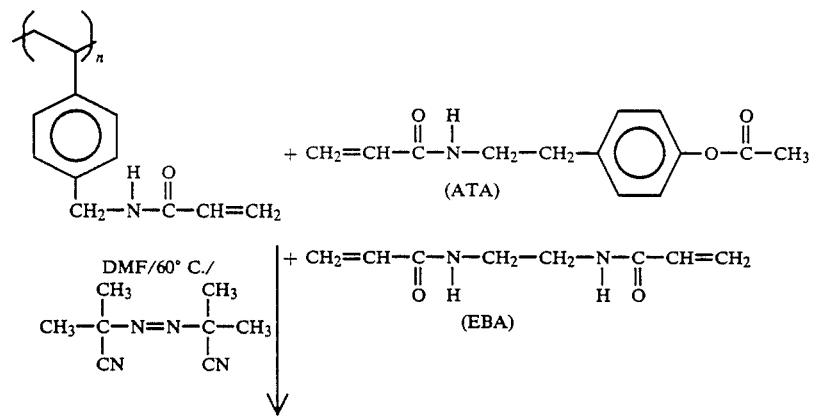

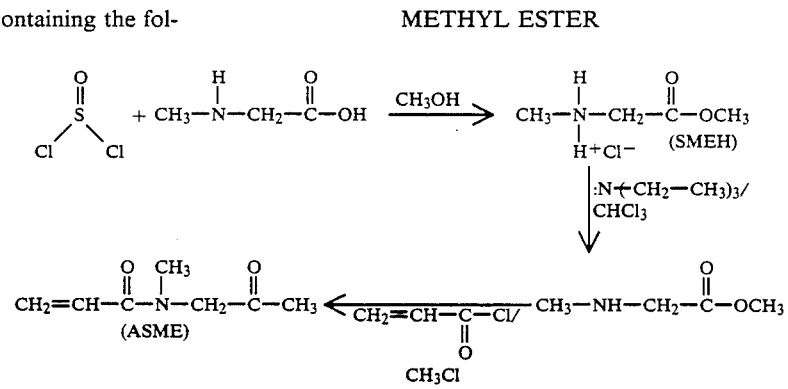

Highly insoluble, cross-linked gel containing the following types of functional group.

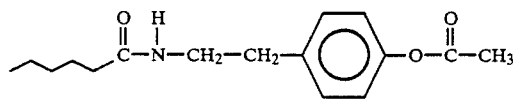

Derivatized porous polymeric material (1.0 g, 0.10 mmol), acryloyl tyramine acetate (ATA) (5 g, 0.03 mol), each as prepared above, N,N'-ethylene bis-acrylamide (EBA, cross-linking monomer) (0.15 g, 0.9 mmol) and azo bis-(iso butyronitrile) (AIBN, free radical initiator) (0.10 g) were placed into a round bottom flask (50 ml) and suspended in the minimum volume of dimethyl formamide (DMF) (15cm³). The reaction mixture was purged with nitrogen for thirty minutes to remove any Methanol (400 ml) was poured into a threeneck, round bottom flask (1 liter) which was placed in a salt/ice bath. Thionyl chloride (32.6 ml, 0.44 mol) was added dropwise to the stirred methanol, over a period of ten minutes. Sarcosine (36 g, 0.4 mol) was added over a period of fifteen minutes and the mixture stirred for twenty minutes before it was allowed to come to room temperature. A condensor was fitted to the flask and the mixture was refluxed for two hours. After cooling, the remaining methanol solvent was removed, using a rotary evaporator, and the residual solid (sarcosine methyl ester hydrochloride, yield, 62 g, 98%) was dissolved in chloroform (500 ml) and dried over magnesium sulphate. The wet magnesium sulphate was removed by filtration and the filtrate divided into two equal volumes (2×250 ml).

One of these portions was poured into a round-bottom flask (1 liter) which was placed in a salt/ice bath. Triethylamine (62 ml, 0.45 mol) was added dropwise to the stirred solution, over a period of ten minutes. Acryloyl chloride (18 ml, 0.22 mol) in chloroform (150 ml) was added to the stirred solution, over a period of fifteen minutes. The mixture was allowed to come to room temperature and the solution was stirred overnight. The mixture was filtered to remove reaction by-products such as triethylamine hydrochloride, and the filtrate diluted (to a total volume of 500 ml) with chloroform. This solution was washed with 10% citric acid (10 ml), 5% sodium bicarbonate (100 ml) and water (100 ml). If the monomer solution was to be retained for any length of time a quinhydrone (0.2 g) stabilizer was added to prevent polymerization. The chloroform solution was dried over magnesium sulphate, filtered to remove the wet magnesium sulphate and the chloroform solvent removed using a rotary evaporator. The product was vacuum distilled at 96.4° C. and 1 mm Hg, taking care to discard the initial few ml of distillate. The final product was a viscous orange/brown liquid which was analyzed by $^1$H nmr. The $^1$H nmr spectrum showed all the peaks and their integral heights to be as anticipated for acryloyl sarcosine methyl ester.

IMPREGNATION OF DERIVATIZED POROUS POLYMERIC MATERIAL WITH ACRYLOYL SARCOSINE METHYL ESTER (15cm$^3$). The reaction mixture was purged with nitrogen for thirty minutes to remove any traces of oxygen which would inhibit the subsequent polymerization. The flask was placed onto a rotary evaporator, with a vacuum, allowed to rotate and lowered into the water bath at 60° C. for two hours. The flask was rotated to hinder polymerization on the surface between adjacent porous polymeric particles and to promote polymerization of ASME within the pores of the porous polymeric material.

The final product was filtered, washed with DMF (3×50 ml), ethanol (3×50 ml) then ether (3×50 ml) and was finally dried in the vacuum oven at room temperature. Since the resulting material consisted of a mixture of different sized particles, the product was ground, using a mortar and pestle and sieved to produce particles in the range 250 to 500 microns in diameter.

Resin II

The method for production is identical to that just described for Resin I above except that the following quantities were used:

| | |
|---|---|
| derivatized porous material | (1 g, 0.01 mmol) |
| ASME | (2 g, 0.01 mmol) |
| DMA | (3.5 g, 0.04 mmol) |
| EBA | (0.5 g, 3 mmol) |
| AIBN | (0.1 g) |

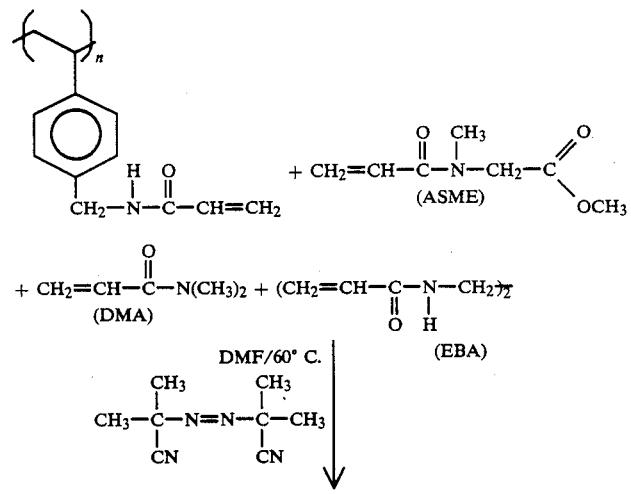

Highly insoluble, cross-linked gel containing the following types of functional group.

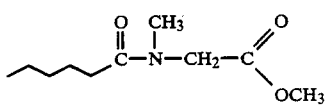

Two types of resin were produced of different loading capacities.

Resin I

Derivatized porous polymeric material (1 g, 0.01 mmol), ASME (0.5 g, 3 mmol), N-N-dimethylacrylamide (DMA) (5 g, 50 mmol), EBA (cross-linking monomer) (0.5 g, 3 mmol) and AIBN (0.1 g) were placed into a round bottom flask (100 ml) and suspended in the minimum volume of dimethyl formamide (DMF)

Both the resins were chemically and physically suitable for use as solid phase supports in peptide synthesis as outlined above.

Resin I had a synthetic capacity of 0.25 mmolg$^{-1}$ and Resin II had a synthetic capacity of 1.00 mmolg$^{-1}$ both measurements being with respect to mmol of peptide synthesized per g of composite substrate. It is of interest to compare these loading capacities with commercially available Kieselguhr based resins having a synthetic capacity of about 0.1 mmolg$^{-1}$.

Each of the present Resin I (0.25 mmol g$^{-1}$) and Resin II (1.00 mmolg$^{-1}$) composite substrates was employed in the synthesis of leucine enkephalin (H-Tyr-Gly-Gly-Phe-Leu-OH). In each case the composite containing reactive sarcosine methyl ester groups, was allowed to react overnight with ethylenediamine to provide primary amine groups throughout the gel.

A reference amino acid derivative Fmoc-Norleucine was coupled to the amine groups by condensation in the presence of dicyclohexylcarbodiimide. Following deprotection (removal of Fmoc) in the presence of 20% piperidine in dimethylformamide, the linkage agent 4-hydroxymethylphenoxyacetic acid was coupled to the exposed amino groups.

The C-terminal amino acid of the desired sequence Fmoc-Leucine was attached to the support by carbodiimide mediated esterification in the presence of a catalytic amount of 4-dimethylaminopyridine. Further cycles of deprotection and coupling were carried out utilizing Fmoc-Phe, Fmoc-Gly, Fmoc-Gly and Fmoc-Tyr (O$^t$Bu) to complete the assembly. All of the steps were performed under continuous flow conditions with the composite packed in a column employing a Pepsynthesiser Mk II ex Cambridge Research Biochemicals.

The following results were obtained:

| | | |
|---|---|---|
| Loading capacity composite (mmol g$^{-1}$) | 0.25 | 1.00 |
| Detachment yield (per 1.0 g composite) | 0.10 g | 0.48 g |
| Purity (by hplc) | 95.3% | 98.2% | hplc = high performance liquid chromatography.

By comparison the theoretical maximum yield from Kieselguhr based supports (e.g. Pepsyn KA available from Cambridge Research Biochemicals) is 0.05 g per 1.0 g composite based on a maximum loading capacity of 0.1 mmol g$^{-1}$ and using the same consumption of solvents and reagents.

The following peptides have also been synthesized using the above described protocol and the composite substrate as described above (Resin II) having a capacity of 1.00 mmol g$^{-1}$.

(i) H-Asp-Asn-Trp-Arg-Ser-Glu-Leu-Tyr-Lys-Tyr-OH
 yield: 1.15 g per 1 g composite
 purity: 98.0%
(ii) H-Val-Pro-Val-Trp-Lys-Glu-Ala-Thr-Thr-Thr-OH
 yield:
 0.98 g per 1 g composite
 purity: 95.1%
(iii) H-Cys-Val-Pro-Thr-Asp-Pro-Asn-Pro-Glu-Glu-Val-Val-OH
 yield: 1.02 g per 1 g composite
 purity: 97.2%
(iv) ACP (65-74) i.e. a segment from acyl carrier protein
 yield: 0.91 g per 1 g composite
 purity: 97.0%

By way of comparison ACP (65-74) was additionally synthesized on control composites of Pepsyn-KA (a kieselguhr based composite having a maximum theoretical loading capacity of 0.1 mmol g$^{-1}$) and batch polystyrene having a maximum theoretical loading capacity of 0.7 mmol g$^{-1}$. The results were as follows:

| Substrate | Yield | Purity |
|---|---|---|
| as in (iv) | 0.91 g | 97.0% |
| Pepsyn-KA | 0.07 g | 96.0% |
| Batch polystyrene | 0.35 g | 35.0% |

EXAMPLE 4

A cross-linked polyvinyl porous polymeric material formed by the high internal phase emulsion method described in U.S. Pat. No. 4,522,953 was employed as the substrate. It had 90% pore volume, a density of 0.047 gcm$^{-3}$ and employed in its preparation 10% cross-linking agent commercial divinyl benzene. The polymeric material was in the form of a milled and sieved powder having a particulate size within the range 850 to 1200 μm. It had a pore size within the range 1 to 50 μm.

The surface of the porous polymeric material was modified as described above by the attachment of the reactive group

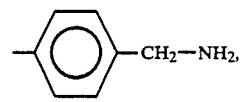

which then served as reactive group X in the peptide synthesis scheme outlined above. Following substantially this peptide synthesis scheme (Fmoc-Leu)$_2$O was employed as the first source of amino acid to be coupled to the substrate. The resulting loading of the amino acid Leu was 0.12 mmolg$^{-1}$ substrate. Removal of the Fmoc group to cause deprotection occurred by use of 20% piperidine in DMF. The acid labile linker

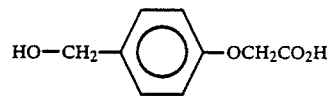

was next coupled to the deprotected amino acid as an active hydroxybenzotriazole ester. Esterification then occurred between the assembly on the substrate and (Fmoc-Gly)$^2$—O in the presence of 0.1 eq. of DMAP. Amino acid analysis of the Gly loading of the substrate was 0.09 mmolg$^{-1}$ substrate. Deprotection next occurred to remove the end Fmoc group and permit subsequent coupling to Ala by use of (Fmoc-Ala)$_2$O.

The resulting peptide assembly had a Gly:Ala ratio of 1:1 indicating a quantitative formation of the desired peptide.

We claim:

1. A substrate comprising a porous cross-linked vinyl polymeric material having a pore structure providing an open porosity of at least 75% and comprising cells having a diameter in the range 1 to 100 μm interconnected by holes and a gel contained and retained in said pore structure by chemical binding to the surfaces of the said polymeric material, said gel being polymeric and having reactive functionality, said cells and holes of said polymeric material having a shape and conformation resulting from polymerization of vinyl material in a high internal phase emulsion system.

2. The substrate according to claim 1, wherein said cells have a diameter in the range of 1 to 50 μm.

3. The substrate according to claim 1, wherein said porous polymeric material has an open porosity in the range 85 to 98%.

4. The substrate according to claim 1, wherein the porous polymeric material is cross-linked to an extent that in use it swells to up to twice its dry bed volume.

5. The substrate according to claim 1, wherein the gel is capable of a loading of reactive residue of from 0.1 to 5 mmol chemical compound synthesized per g of substrate.

6. The substrate according to claim 1, wherein said gel is chemically bound to said porous polymeric material by an amide linkage.

7. The substrate according to claim 1, wherein the ratio by weight of swollen gel to porous polymeric material lies in the range 60:40 to 95:5.

8. A substrate comprising a porous cross-linked vinyl polymeric material having a pore structure providing an open porosity of at least 75% and comprising cells having a diameter in the range 1 to 100 $\mu$m interconnected by holes and a gel contained and retained in said pore structure by interaction with the surfaces of the said polymeric material, said gel being polymeric and having reactive functionality, said cells and holes of said polymeric material having a shape and conformation resulting from polymerization of vinyl material in a high internal phase emulsion system.

9. The substrate according to claim 8, wherein said cells have a diameter in the range 1 to 50 $\mu$m.

10. The substrate according to claim 8, wherein said porous polymeric material has an open porosity in the range 85 to 98%.

11. The substrate according to claim 8, wherein the porous polymeric material is cross-linked to an extent that in use it swells to up to twice its dry bed volume.

12. The substrate according to claim 8, wherein the gel is capable of a loading of reactive residue of from 0.1 to 5 mmol chemical compound synthesized per g of substrate.

13. The substrate according to claim 8, wherein the gel is retained within the pores of the porous polymeric material by chain entanglement between the gel and the porous polymeric material.

14. The substrate according to claim 8, wherein the ratio by weight of swollen gel to porous polymeric material lies in the range 60:40 to 95:5.

* * * * *